United States Patent
Evans et al.

(10) Patent No.: US 7,785,569 B2
(45) Date of Patent: Aug. 31, 2010

(54) LYOPHILIZED EDIBLE FOOD INCORPORATING A MARKER

(75) Inventors: Keith Darrel Evans, Brentwood, TN (US); Stanley John Konopka, Franklin, TN (US); Kerry Clepper Bush, Brentwood, TN (US)

(73) Assignee: Advanced Breath Diagnostics, LLC, Brentwood, TN (US)

( * ) Notice: Subject to any disclaimer, the term of this patent is extended or adjusted under 35 U.S.C. 154(b) by 786 days.

(21) Appl. No.: 10/435,092

(22) Filed: May 9, 2003

(65) Prior Publication Data

US 2003/0211042 A1 Nov. 13, 2003

Related U.S. Application Data

(60) Provisional application No. 60/379,581, filed on May 10, 2002.

(51) Int. Cl.
*A61K 49/00* (2006.01)
*A61K 51/00* (2006.01)
*A61K 35/54* (2006.01)
*A61K 9/00* (2006.01)

(52) U.S. Cl. .................. 424/9.2; 424/1.61; 424/195.17; 424/581

(58) Field of Classification Search .................. None
See application file for complete search history.

(56) References Cited

U.S. PATENT DOCUMENTS

| 4,985,232 | A | | 1/1991 | Jacobssen | 424/4.1 |
| 5,707,602 | A | * | 1/1998 | Klein | 424/1.17 |
| 5,785,949 | A | | 7/1998 | Klein | 424/1.81 |
| 6,432,382 | B1 | | 8/2002 | Mehta | |
| 6,548,043 | B1 | | 4/2003 | Wagner et al. | |
| 6,740,305 | B1 | | 5/2004 | Ajami | |

FOREIGN PATENT DOCUMENTS

| GB | 2360845 A | * | 10/2001 |
| WO | WO 97/35622 | | 10/1997 |
| WO | WO 01/72342 | | 10/2001 |

OTHER PUBLICATIONS

J S Lee, et al., "A Valid, Accurate, Office Based Non-Radioactive Test for Gastric Emptying of Solids" Gut 2000; 46:768-773.
B.E. Viramontes, et al., "Validation of a Stable Isotope Gastric Emptying Test for Normal, Accelerated or Delayed Gastric Emptying" Neurogastroenterol. Mot. (2001) 13, 567-574.
Yvo F. Ghoos, et al., "Measurement of Gastric Emptying Rate of Solids by Means of a Carbon-Labeled Octanoic Acid Breath Test" Gastroenterology 1993;104:1640-1647.

* cited by examiner

*Primary Examiner*—Lisa J Hobbs
(74) *Attorney, Agent, or Firm*—Fredrickson & Byron, P.A.

(57) ABSTRACT

A standardized, lyophilized edible food containing a biologically safe stable marker for use in the measurement of gastric emptying by the quantification of marker excreted in the breath of the patient.

17 Claims, No Drawings

LYOPHILIZED EDIBLE FOOD INCORPORATING A MARKER

CROSS REFERENCE TO RELATED APPLICATIONS

This application is entitled to the benefit of provisional patent application No. 60/379,581 entitled "Lyophilized Edible Foods for Use in Medical Tests," filed May 10, 2002, and incorporated herein by reference.

FIELD OF THE INVENTION

This invention relates generally to a lyophilized (freeze-dried) meal including an edible food, a component of which includes a marker or drug and methods for using same for reliably delivering a marker or drug into a mammal and the use of that meal for measuring the absorption of therapeutic and diagnostic drugs or markers across an array of highly standardized meals. It also relates to a method of validating a meal to be used in diagnostic or test methods. Furthermore, the meal may be used to measure bodily (physiological) functions as a result of the digestion, absorption and/or metabolism of the meal and its marker or drug.

BACKGROUND OF THE INVENTION

Digestion of consumed foodstuffs begins in the oral cavity where food is mechanically broken down by mastication, lubricated with saliva, and enzymatically processed by amylase present in the saliva. Digestion continues in the stomach where food is liquefied by gastric juices and enzymes secreted by the cells lining the stomach to produce chyme. Chyme enters the small intestine via the pyloric sphincter for further processing by bile salts produced by the liver and pancreatic digestive enzymes. Components not absorbed by or transported into the small intestine are subject to subsequent processing in the large intestine.

The rate at which chyme travels to the small intestine (gastric emptying rate) is the product of numerous physiological factors including, hormones, chemical signals in the ingesta, as well as signals from the nervous system.

A number of the population are affected by disorders that affect the emptying rate. For example, when the rate is accelerated, undigested food is prematurely dumped from the stomach to the small intestine. Conversely, when the rate is decelerated, the movement of ingested food from the stomach to the small intestine is delayed, giving rise to the condition termed "delayed emptying" otherwise known as gastroparesis.

Disorders involving gastric emptying rate are typically diagnosed by monitoring the rate at which a meal empties the stomach and enters the small intestine. In these tests, typically, an edible food is used to transport a marker into the gut of an animal and gastric emptying monitored by the marker.

Currently, the routine method for quantifying gastric emptying in humans is quantitative scintigraphy. Scintigraphy involves the ingestion of a meal including at least one edible food, a component of which has been radiolabeled and the subsequent measurement of gamma emission by a scintillation camera as the labeled food is emptied from the stomach.

The most common type of meal used in scintigraphy measurement of gastric emptying is a meal typically made by cooking 0.5 mCi $^{99m}$Tc sulphur colloid with two raw eggs or 120 grams of a liquid egg substitute such as the product sold by ConAgra under the trademark Egg Beater®. In typical use, the patient fasts the night before the test. At the time of the test the patient consumes the cooked radiolabeled egg component with two slices of bread, 30 grams of jam and 120 ml of water. Scintigraphic scanning with anterior and posterior cameras is performed immediately after the test meal is consumed and scans are obtained every 15 minutes for two hours and every 30 minutes for up to six hours. Scintigraphy measurements of gastric emptying are direct, since the camera directly measures the meal exiting the stomach.

In the measurement of gastric emptying, two parameters are clinically useful. The first, $t_{LAG}$, is the time required for the first 10% of the food to empty from the stomach. The second, $t_{1/2}$, is the time required for half of the contents to be emptied from the stomach. Percent gastric retention of the radiolabel is calculated at each time point to generate a scintigraphic gastric retention curve. The curve is mathematically modeled with a power exponential model and the diagnostic result $t_{LAG}$ and $t_{1/2}$ can be calculated from the curve.

Several disadvantages are associated with the traditional scintigraphy method. First, patients must be subjected to radioisotopes. This is particularly problematic for women of childbearing age or children. Further, the procedure must be carried out at specialized nuclear medicine facilities. Finally, the preparation for the procedure is cumbersome and potentially can introduce error to the test procedure. Prior to the procedure, personnel must prepare the labeled meal. Because cooking parameters or food quality may vary from hospital to hospital, standardization is lacking. As with any medical test, standardization is of significant importance in gastric emptying test procedures.

Recently, a method for measuring gastric emptying has been described that utilizes an edible food labeled with non-radioactive markers. As the non-radioactive labeled edible food is digested, a labeled component is produced which can be detected in the patient's breath. This method is described in detail in U.S. Pat. No. 5,707,602, the teachings of which are hereby incorporated by reference. This patent describes the use of a nutritional supplement, *Spirulina platensis*, a blue green algae, grown in a highly enriched $^{13}CO_2$ environment. The $^{13}$Carbon acts as a non-radioactive marker. A small amount of the labeled algae is baked into a roll or breakfast bar and consumed by a patient with juice or water. The meal is triturated by the stomach to a particle size of approximately 1-2 mm and then passes from the stomach through the pylorous into the intestine. In the intestine, the labeled products of $^{13}$C-*Spirulina platensis* digestion are absorbed and metabolized giving rise to labeled carbon dioxide expired in the breath. The rate of $^{13}CO_2$ appearance in the patient's breath ($^{13}CO_2$ excretion rate) is correlated to the rate of gastric emptying.

In contrast to scintigraphy, measurement of gastric emptying, in accordance with the marker described above, is indirect. Therefore, it is desirable to mathematically correlate the $^{13}CO_2$ excretion curve to the scintigraphic gastric retention curve so that the emptying time of the stomach can be calculated from the $^{13}CO_2$ curve. For example, one can use a general linear model to develop the relationship between diagnostic parameters obtained from scintigraphic measurements and the corresponding data obtained from the patient's $^{13}CO_2$ excretion rate when both the radioactive scintigraphic label and $^{13}$C-label are administered simultaneously in the same meal.

To accurately correlate the $^{13}CO_2$ excretion curve and the scintigraphic decay curve, it is desirable to standardize the edible food and/or meal matrix delivering the marker to reduce the number of variables. For example, if the new marker or drug (the surrogate) is incorporated into an edible food and/or meal (surrogate meal) that is different than the edible food and/or meal in which the well accepted marker or drug (predicate) is incorporated (predicate meal) the correlation process may be more difficult. Thus, it is desirable for the predicate and surrogate meals to be as similar in composition, texture and nutritional content to each other as possible.

Similarly, such standardization allows for the validation of novel diagnostic or medical tests against well known, accepted tests ensuring accuracy and acceptance within the medical community. This may be particularly important where the new test detects, assesses, or measures physiological characteristics in a different manner, for example, indirectly versus directly.

In addition to standardization between novel and traditional medical tests, it is desirable that each individual method be standardized. It is desirable and often essential, that a medical test be performed identically each time it is conducted.

Thus, it is an object of the present invention to ensure reliability and standardization when delivering a meal combined with a marker or therapeutic drug into or beyond the stomach. It is further an object to provide a reliable method of validating and measuring the absorption and/or activity of the drug or marker.

SUMMARY OF THE INVENTION

One embodiment of the invention comprises a freeze-dried (lyophilized) edible food comprising a marker or drug for delivering the marker or drug as part of a meal to be consumed by a mammal in order to assess a bodily function, diagnose a condition or other such medical application.

Another aspect of the invention is a method for validating the use of a surrogate marker or drug as a component of an edible food in a surrogate or predicate meal as a means of assessing a particular bodily function or diagnosing a particular medical condition comprising providing a lyophilized predicate meal, said predicate meal comprising a first marker or first drug which predicate meal has been validated for use in a medical test and providing a lyophilized surrogate meal, said surrogate meal comprising a second marker or second drug chosen for use with the surrogate meal in the medical test wherein the predicate meal and surrogate meal without the marker or drug are matched in physiological and metabolic behavior.

Yet another aspect is a method of measuring gastric emptying utilizing a standardized, freeze-dried meal incorporating a marker that is mathematically correlated to a bodily function to be evaluated.

DETAILED DESCRIPTION OF THE PREFERRED EMBODIMENT

A standardized gastric emptying test that is safe, efficient, and that can be readily used in a clinical setting may employ a stable marker such as $^{13}C$ incorporated into a prepared standardized meal. A standardized freeze-dried meal uniformly labeled, easily re-constituted surrogate meal will assure more reliable performance of the test for which the meal is prepared. The terms freeze dry and lyophilize are used interchangeably herein.

The standardized meal into which the marker is to be incorporated may be any food type suitable for human consumption. For example, typical meals used for gastric emptying tests have included scrambled eggs and liver. As will be appreciated by those skilled in the art, any food item that is amendable to the freeze dry process may be utilized. Food items can be chosen to accommodate patients with special dietary needs, for example, vegetarians or those desiring food processed under Kosher standards.

In one embodiment, the standardized meal is eggs. Traditional scintigraphy methods have provided a meal consisting of a sandwich prepared with radio labeled eggs. Recent studies indicate that the excretion curve derived from a biologically labeled meal correlates well with the gamma emission curve. Further, eggs are amendable to the freeze drying process and have a long shelf life.

The meal or edible food component of a meal can be labeled with a stable, biologically safe isotope, such as $^{13}C$. As will be appreciated by those skilled in the art, $^{13}C$ may be provided from any source that is suitable for human consumption. For example, octanoic acid incorporating $^{13}C$ may be mixed with the meal or edible food component of a meal. In one embodiment, the source of the $^{13}C$ is S. platensis. Algae containing $^{13}C$ may be obtained by growing the algal cells in a $^{13}C$-enriched environment as is disclosed in commonly assigned pending U.S. application Ser. No. 10/417,951, METHODS OF PRODUCING CARBON-13 LABELED BIOMASS, filed Apr. 16, 2003, the disclosure of which is herein incorporated by reference in its entirety.

The freeze-dry standardized meal can be used with a variety of markers and applied to a wide array of meal types and incorporate all types and exacting amounts of markers, including those that are directly synthesized with $^{13}$Carbon label or those derived through biomasses like $^{13}C$-S. platensis.

To ensure accuracy of test results, the $^{13}C$ is desirably uniformly distributed throughout the edible meal or food component thereof. In one embodiment, the meal or component thereof and $^{13}C$ algae are lyophilized separately. Subsequently, a pre-measured amount of $^{13}C$ algae is thoroughly mixed with a pre-measured amount of lyophilized egg to ensure uniform distribution. Alternatively, a pre-measured amount of algae containing $^{13}C$ can be thoroughly mixed with a pre-measured amount of egg prior to lyophilization. In this embodiment, no onsite preparation other than reconstitution and cooking, if necessary, is required.

As will be appreciated by those skilled in the art, the amount of algae or other source of $^{13}C$ to be added to the meal or component thereof will depend on a variety of factors including desired dosage, the amount of meal material, and the source of $^{13}C$. It is apparent that a plurality of meals can be produced simultaneously according to the freeze dry method. Once the marker is uniformly distributed in a meal or component thereof, individual servings can be produced by simply dividing the batch by weight, volume, or any other suitable technique, into individual servings.

There are several advantages to using a freeze-dry process to prepare standardized meals. Freeze-dried meals provide a vehicle of reliably and accurately incorporating a marker such as a stable isotope labeled material or drug into a edible food matrix. The marker or drug may be incorporated into the edible food during preparation or at the site where the meal will be re-constituted. Freeze-dried meals also assure standardization of tests across all medical users and sites of administration. Various biological markers or drugs, and combinations thereof, can be incorporated and evaluated from the same meal matrix. Refrigeration is not required for freeze-dried meals, which makes them easier to store and prevents spoilage.

It should be understood that the lyophilized delivery meal may be utilized to effectively and accurately incorporate and deliver any marker, isotope, or drug that is not susceptible to degradation during the lyophilization process so that the marker or drug maintains its functional activity once the delivery meal is reconstituted. Freeze-drying a standard meal wherein a marker or drug may be incorporated into one component of the meal may be used to deliver a marker or drug for use in any medical procedure where a physiological measurement is made following ingestion of a labeled edible food by the patient.

The standardized freeze dried meal may be used to assess gastric emptying in patients or test subjects. To utilize the meal, the clinical personnel simply reconstitute the pre-labeled meal prior to the test. The patient then ingests the meal including the marker, for example, labeled algae. As the patient empties the meal to the small intestine, the $^{13}C$ is absorbed and oxidized to $^{13}CO_2$. The $^{13}CO_2$ is excreted in the breath of the patient. Breath samples are collected by techniques known in the art, at periodic time intervals and the amount of $^{13}CO_2$ in the breath sample determined by techniques known in the art.

For accurate results, the marker must remain bound to the delivery vehicle, for example, an edible food component. If the marker becomes unbound it may move out in front of the solid phase emptying process into the liquid phase, passing through the pylorus and into the intestine faster than is representative of the actual gastric emptying process. It may also pass through the stomach wall and enter the circulation and metabolism process in a manner that gives rise to a $^{13}CO_2$ signal unrelated to the digestive process intended to be measured. Thus, it is important to ensure that the manufacturing process does not change the nature of raw materials to the extent that binding capacity is lost.

In diagnostic tests using $^{13}C$, the amount of $^{13}C$ administered must be precisely known. In a breath test, the results are based on the amount of $^{13}CO_2$ produced, which is directly related to the amount originally ingested. To determine the actual dosage of $^{13}C$, it is necessary to know the weight percentage of total carbon, as well as the percent of $^{13}C$. This is shown in Table 1, which illustrates three different amounts of $^{13}C$ label target dosages for the $^{13}C$-labeled algae species $S.$ $platensis$. The amount of $^{13}C$ labeled $S.$ $platensis$ that must be incorporated into a meal to achieve the target dose of $^{13}C$ is determined according to the following equation:

Target dose mg $^{13}C/(^{13}C$-Atom % Carbon %)=mg [$^{13}C$]-$S.$ $platensis$ dispensed Table 1 provides several examples of how the equation is used. This calculation is applicable to $^{13}C$-labeled molecules or larger entities, such as a biomass.

TABLE 1

Example calculation of dispensing to achieve three target dose levels of $^{13}C$.

| Target Dose Mg.$^{13}C$ | [$^{13}C$]-$S.p.$ $^{13}C$-Atom % | [$^{13}C$]-$S.p$ % Carbon | [$^{13}C$]-$S.p.$ mg | Tolerance ± mg |
|---|---|---|---|---|
| 80 | 0.95 | 0.42 | 200 | 20 |
| 40 | | | 100 | 10 |
| 20 | | | 50 | 5 |

For $S.$ $platensis$, the carbon content will generally be about 42%, and the $^{13}C$ incorporation about 95%, as shown in the table above.

One may now perform a study with a sufficient number of patients to establish appropriate dosage to be added to a standardized meal. A specific example is to conduct a prospective cross-over study where a set of normal patients and a set equal in number of patients with known delayed gastric emptying are each administered the same meal 3 times on separate occasions with the meal remaining the same except for a different dosage of $^{13}C$ label as prescribed in the table above. The area under the $^{13}CO_2$ excretion curves from the normal and delayed emptying groups can be compared at the 3 different dose levels with appropriate statistical challenges to determine the lowest acceptable dose that provides sufficient signal to assess both normal and impaired (delayed) gastric emptying utilizing the intended meal. The can then be consistently produced containing the selected dosage.

Under circumstances where the marker or source of the marker and/or meal or component thereof is changed, it is desirable to validate the new (surrogate) marker or food. To fully validate the use of such a breath test among all pertinent patient populations, it is necessary to correlate the results obtained with the results that would be obtained using the scintigraphy test. Differences in the type of meal or marker used may give rise to different gastric emptying rates and different physiologic and metabolic footprints. While a mathematical relationship between the two meals may be established and the surrogate meal become a reliable predictor for $t_{1/2}$, the number of studies necessary to validate the relationship will be increased and it is possible that a consistent relationship will not occur between the predicate meal and the surrogate meal across all patient populations if the composition of each meal is significantly different. For example, in gastric emptying tests it is possible that two different meals or markers may have a consistent mathematical and physiological relationship in normal patients, but perhaps not in some affected patients. A high number of gastroparetics (late dumpers) are diabetic and diabetics may metabolize different meals in a manner that gives rise to some inconsistency in the predicted relationship between two different meals.

Simply matching the protein, carbohydrate and fat content of the surrogate meal to the predicate meal will not assure physiological consistency. The type of protein, carbohydrate and fat content may be different, i.e., the protein in the egg meal may be primarily albumin, whereas the roll may contain primarily soy protein. Hence, the matrix binding the labels is different and subtle but important differences in trituration, absorption, and metabolism of the surrogate marker or drug may occur that will affect the proper classification of a patient.

To improve reliability in the validation process, the surrogate meal should match the predicate meal. In order for such a surrogate meal intended for widespread outpatient utilization to be highly reliable, safe and easily distributed it should be consistent in texture, composition and nutritional value to the predicate meal; have a consistent physiological and metabolic relationship to the predicate meal used to determine its efficacy; be safe from spoilage and decay; and have a commercially reasonable shelf life prior to utilization.

In an embodiment of the invention where a meal is used for assessing gastric emptying, both the predicate $^{99m}Tc$ label or meal and the surrogate marker or meal may be incorporated into the same meal matrix. In this case the $^{99m}Tc$ label must be added to the meal matrix at the site of administration due to its short radioactive-½ life-nature.

In one embodiment of the invention, the predicate meal is provided as the lyophilized standard pre-labeled meal described above. After the predicate meal is reconstituted, $^{99m}Tc$ label is added so that the radiolabel and surrogate marker are bound in the same food matrix. The patient or test subject then ingests the dual labeled meal and gastric emptying is measured simultaneously by the scintigraphy method previously described and the breath test. The two measurements thus obtained are compared against each other and mathematically correlated. Since both the radiolabel and surrogate marker are incorporated into the same matrix, this embodiment allows for the reliable validation of a predicate meal type or predicate marker.

One advantage of establishing a lyophilized meal suitable for introduction of both a predicate and surrogate marker is that the meal may be used to test different dosages of labels to assure that there is sufficient label signal arising from the meal to make the appropriate physiologic or diagnostic conclusion. For example, prior to establishing a relationship between an established radioactive predicate label and a new non-radioactive $^{13}C$ surrogate label, the appropriate dose of $^{13}C$ to be incorporated in the meal to provide a reliable $^{13}CO_2$ excretion rate in the patient. The signal must be readily measurable providing reliable data from which to establish the mathematical relationship between the predicate and surrogate marker.

According to another embodiment, both a surrogate meal and predicate meal are prepared according to the lyophilization process described above to prepare a surrogate meal matching a like-prepared predicate meal. In this embodiment, meals having identical edible food components (that is, the same edible food in the same amounts in each meal, prior to the incorporation of any label into the meal) containing no marker is reconstituted and the predicate label and surrogate marker are each added at the time of reconstitution. Both the predicate meal and the surrogate meal intended to be tested in clinical studies will be prepared with the same pre-label contents and in the same manner. Alternatively, if the surrogate label is stable, that is, capable of maintaining its functional activity, it may be added to a meal prior to lyophilization. Since two meals are compared the patient or test subject will ingest each meal at different times and the results mathematically correlated.

The development of a surrogate meal that can be used to reliably validate the use of a surrogate marker or drug that is similar in texture, composition and nutritional value to a predicate meal and that may be readily incorporated into a commercially available meal/delivery system will allow for the substitution of stable non-radioactive labels for radioactive labels in test meals. Thus, in assessing physiological conditions such as gastric motility in women of childbearing age and in children where radiation exposure is undesirable, stable, non-radioactive markers may be used.

A multitude of assessments may be done using the gastric emptying markers described herein such as predicate and surrogate marker comparisons, measurement of intra-patient gastric motility variation, inter-patient comparisons, and the like.

Ideally, the edible foods of the surrogate, predicate, or meals used in the clinical setting of the invention are prepared in a controlled food and/or pharmaceutical manufacturing environment meeting appropriate regulatory standards with long term packaging stability and with easy and reliable re-constitution techniques. The preparation of these meals in a manufacturing environment of this type ensures that the raw materials of the meals will not be randomly prepared at the site of test administration, which may lead to inaccuracies. For example, inconsistencies may arise from site to site due to differences in grocery type supplies, differences in cooking methods and times, and test administration techniques. Further, the use of a manufacturing process to prepare the edible food is beneficial because it allows not only for the production of a more "standardized" meal, but for wide scale commercial use of the edible foods with an appropriate biological marker or drug. For those meals that must be cooked at the testing site, it is best that the same method of cooking be applied to the predicate meal and the surrogate meal to minimize uncertainty.

A freeze-dried standardized meal of the invention can serve as a standardized delivery mode for therapeutic drugs. Similarly an array of freeze-dried standardized meals of the invention can be used to study the absorption of various diagnostic and/or therapeutic drugs with varying meal compositions. Further, a freeze-dried standardized meal incorporating markers and/or therapeutic and diagnostic drugs can be used for animal studies in which food components, dosage of label or drug and amount of food by weight must be delivered with reliable control. In an embodiment of the invention, once a surrogate meal with its surrogate marker or drug has been established as useful by comparison to a predicate meal with the predicate marker or drug, freeze drying the edible food components of the meal ensures not only the stability of the meal but the reproducibility of the test results obtained with such standardized meals.

While several embodiments described herein show the use of a freeze-drying method of preparing the edible foods of the meals, it would be apparent to one skilled in the art that any method guaranteeing that the surrogate meal is identical in composition to the predicate meal can be used. For example, the edible food components may be prepared by baking of the edible components into a roll or biscuit in accordance with a standardized process and the predicate marker or drug and the surrogate marker or drug may be incorporated into the meal during a controlled manufacturing process or at the site of the test.

The invention will be further described with reference to the following non-limiting Examples. It will be apparent to those skilled in the art that many changes can be made in the embodiments described in the Examples without departing from the scope of the present invention. Thus, the scope of the present invention should not be limited to embodiments described in this application, but only by the embodiments described by the language of the claims and the equivalents of those embodiments.

EXAMPLE 1

Preparation of $^{13}C$ Pre-Labeled Standardized Egg Meals 207.41 kg (amount required to prepare 2,000 meals) of pasteurized, de-sugared whole egg liquid formula containing whole eggs, water, nonfat dry milk, salt, and smoke flavoring was thoroughly mixed with 200 g of $^{13}C$-labeled *S. platensis* containing 95% atom % $^{13}C$ and 42% total carbon. The amount of liquid egg formulation required to produce a specific number of meals of 28 g was calculated from the following equation:

(Amount of units)×(28 g/0.27)=grams of liquid egg formulation.

The necessary amount of labeled algae depends on the percentage of $^{13}C$ present in the algal cells and was calculated from the following equation:

$^{13}C/(^{13}C$-atom %×Carbon %)=mg[$^{13}C$]-*S. platensis*

The total amount of labeled algae required was calculated by the following equation:

Number of doses×mg[$^{13}C$]-*S. platensis*/dose

The liquid egg formulation containing the appropriate amount of thoroughly mixed label was pumped onto pre-chilled anodized aluminum lyophilization trays and lyophilized for 24 hours with a initial temperature of −20° C. and a final temperature of 48° C. under <200 microns of pressure, to meet a loss on drying (LOD) specification of <3.0% moisture content. The resulting freeze-dried labeled mixture was divided to produced 2,000 units of meals of uniform weight and label distribution.

EXAMPLE 2

Confirmation of Uniform Distribution of Marker

Ten samples were randomly pulled from approximately the beginning, middle, and end points in the milling process from a manufacturing run that was prepared to produce units each containing 6 mg. $^{13}$C derived from [$^{13}$C]-S. platensis. An aliquot of each sample was analyzed in a combustion chamber attached to an isotope ratio mass spectrophotometer and compared to a known $^{13}$C standard.

The samples had a mean recovery of 6.01 mg per sample, a standard deviation of 0.072, and a % relative standard deviation of 1.19%. These results demonstrate that the $^{13}$C label was uniformly distributed in the meal matrix.

EXAMPLE 3

Confirmation of Uniform Distribution of Marker in Meals Prepared On-Site

In some instances it may be desirable to provide the freeze dried meal and label separately so that the label may be mixed with the meal just prior to use. However, uniform distribution of the label remains of significant importance.

To determine whether manual, on-site mixing yields acceptable uniform distribution of the marker a quantity of [$^{13}$C]-S. platensis and liquid egg formulation were freeze-dried separately as described above. A 50 mg aliquot of dried [$^{13}$C]-S. platensis was rehydrated in 5 g of water in a 20 mL glass vial with a Teflon lined screw cap for 10 minutes and added to 28 g of egg powder. 88 g of water was used to rinse the content of the rehydration vial into the egg mix, the mixing container capped, and shaken vigorously for 1 minute. The egg mix was cooked in a microwave for 1.5 minutes, allowed to cool, and separated into 6 samples. The above meal preparation was done in triplicate.

Each of the 6 slices of each the 3 meals were dried and into uniform samples via mortar and pedestal. An aliquot was removed from each sample and combusted and assayed by gas isotope ratio mass spectrometry and the amount of $^{13}$C determined by comparison to a known standard.

The % relative standard deviation across the 6 samples from each of the 3 meals was 5.2%, 3.4%, and 3.3% respectively. These results demonstrate that on-site mixing produced meals with uniformly distributed marker.

EXAMPLE 4

Evaluation of Binding Capacity 28 g of lyophilized egg powder containing a known quantity of $^{13}$C-marker was reconstituted with 93 g of water, mixed, and cooked. The cooked meal was cooled, weighed and pressed through a 4 mm screen into a collection pan. Ten gram samples were collected, dried overnight at 105° C., and ground by mortar and pestle into a fine powder. Duplicate aliquots of the dried sample were combusted and assayed by gas isotope ratio mass spectrometry.

Eighty percent of the portion of egg meal that remained in the pan after the screening procedure was divided into 2 equal amounts and subjected to in vitro digestion. U.S.P. gastric fluid was prepared by dissolving 2.0 g of NaCl$_2$ and 3.2 g of purified pepsin derived from porcine stomach mucosa with an activity of 800-2500 units/mg protein in 7.0 mL of hydrochloric acid. The volume was brought to 1 L with water and the pH brought to approximately 1.2.

The egg meal portions were incubated in 100 mL of the prepared gastric solution at 37° C. for 30 minutes with constant stirring at a fixed rate of 200±20 rpm using a stainless steel paddle apparatus located approximately 0.25 in from the bottom of the flask. After digestion, the contents of each flask were poured over a stacked set of 4 mm, 2 mm, and 1 mm screens and rinsed with cool tap water for 1 minute at a rate of approximately 4 L/min and the screening stack allowed to drain for 5 minutes.

The weight of digested meal remaining on each screen was recorded and isolated in tared aluminum sample pans. The samples were air dried over night at 105° C. to remove excess water. An aliquot of the 1 mm sample (representative of the smallest size a food particle reaches after the full trituration process) was analyzed for $^{13}$C by combustion and assay by ratio mass spectrometry and compared to the pre-digestion $^{13}$C amounts. The percent binding was calculated according to the following equation:

($^{13}$C content per gram of Carbon post-digested meal)/ ($^{13}$C content per gram of Carbon pre-digested meal)×100.

Percent binding was 100% in the 1 mm digested samples compared to the pre-digested samples with 51% of the overall egg mass lost during in vitro digestion.

While preferred embodiments of the present invention have been described, it should be understood that various changes, adaptations and modifications may be made therein without departing from the spirit of the invention and the scope of the appended claims.

What is claimed is:

1. A lyophilized product comprising lyophilized whole eggs, wherein both egg yolk and egg white of the whole eggs are bound to a known amount of a $^{13}$C marker derived from a biomass, said $^{13}$C marker chosen so that when ingested by a mammal with a meal either the absorption or metabolism of the marker may be monitored and correlated to a physiological function of the mammal.

2. The product of claim 1, wherein during trituration in a mammal's stomach substantially all of the $^{13}$C marker remains bound to the whole eggs.

3. The product of claim 1, wherein the whole eggs are part of a liquid egg formulation prior to being lyophilized.

4. The product of claim 3, wherein the $^{13}$C marker is thoroughly mixed with the liquid egg formulation prior to being lyophilized.

5. The product of claim 1, wherein the $^{13}$C marker is uniformly distributed throughout the whole eggs.

6. The product of claim 1, wherein the biomass is $^{13}$C-enriched Spirulina platensis.

7. The product of claim 1 wherein the product is packaged into a unit dose form.

8. The product of claim 1, wherein the physiological function is a metabolic function.

9. The product of claim 1, wherein the physiological function is a digestive function.

10. The product of claim 1, wherein the physiological function is the rate of gastric emptying.

11. A lyophilized product comprising:
lyophilized whole eggs;
a known amount of $^{13}$C-enriched *Spirulina platensis* uniformly distributed throughout the lyophilized whole eggs;
wherein both egg yolk and egg white of the whole eggs are bound to the $^{13}$C-enriched *Spirulina platensis*.

12. The product of claim 11, wherein the whole eggs are part of a liquid egg formulation prior to being lyophilized.

13. The product of claim 12, wherein the $^{13}$C-enriched *Spirulina platensis* is thoroughly mixed with the liquid egg formulation prior to being lyophilized.

14. The product of claim 11 wherein the product is packaged into a unit dose form.

15. The product of claim 11, wherein the product is for use in tests that monitor a physiological function of a mammal.

16. The product of claim 11, wherein the product is for use in tests that monitor a digestive function of a mammal.

17. The product of claim 11, wherein the product is a gastric emptying product for use in tests that monitor the rate of gastric emptying.

* * * * *